United States Patent [19]

Wood et al.

[11] Patent Number: 5,766,211
[45] Date of Patent: Jun. 16, 1998

[54] MEDICAL DEVICE FOR ALLOWING INSERTION AND DRAINAGE INTO A BODY CAVITY

[76] Inventors: Jan Wood, 6408 Shetland Ct., Mobile, Ala. 36695; Cheryl Flock, 31 S. Monterey St., Mobile, Ala. 36604

[21] Appl. No.: 644,421

[22] Filed: May 10, 1996

Related U.S. Application Data

[63] Continuation-in-part of Ser. No. 295,993, Aug. 24, 1994, which is a continuation of Ser. No. 14,657, Feb. 8, 1993, abandoned.

[51] Int. Cl.[6] ............................................. A61M 1/00
[52] U.S. Cl. ........................... 604/32; 604/30; 604/284
[58] Field of Search .............................. 604/28, 30, 32, 604/35, 83, 86, 244–248, 256, 283, 284

[56] References Cited

U.S. PATENT DOCUMENTS

| | | |
|---|---|---|
| 2,854,027 | 9/1958 | Kaiser et al. |
| 4,219,021 | 8/1980 | Fink. |
| 4,758,235 | 7/1988 | Tu ............................................. 604/248 |
| 4,950,230 | 8/1990 | Kendell ........................................ 604/28 |

*Primary Examiner*—Robert A. Hafer
*Assistant Examiner*—N. Kent Gring
*Attorney, Agent, or Firm*—Gregory Friedlander

[57] ABSTRACT

The invention is an irrigating device having a rigid housing defining a canal containing a three way valve selecting between three ends where at least one of the three stems has an elastic attachment for receiving two separate non-elastic medical input devices sharing a common chamber which common chamber communicates with the rigid housing canal. It has at least one three-way valve directing the flow of suction or fluids to graduated openings in the medial, distal and proximal direction. The medial opening is where the elastic attachment is place which defines a plurality of tubes. All of these tubes may be elastic. All may have an inner circumference for receiving a tube or syringe of corresponding outer diameter. Alternatively, one of these tubes may be elastic having an outer diameter for insertion into a tube or syringe of corresponding inner diameter so as to form an elastic, but water tight seal.

17 Claims, 5 Drawing Sheets

MEDICAL DEVICE FOR ALLOWING INSERTION AND DRAINAGE INTO A BODY CAVITY

PRIORITY HISTORY

This application is a continuation in part of the pending prior application Ser. No. 08/295,993 filed Aug. 24, 1994 now pending which was a continuation of Ser. No. 08/014,657 (abandoned) which was filed Feb. 8, 1993.

BACKGROUND OF THE INVENTION

This invention relates broadly to the art of irrigation and suction.

The invention relates to a portable lavage adapter designed to instill medication or fluid and/or withdraw irrigating fluid from a body cavity either through gravity drainage or suction.

Gastric lavage, the most common type of lavage, is the irrigation of the stomach using an appropriate liquid. Lavage is carried out using room temperature normal saline that is instilled into the nasogastric tube. The Fluid is then either aspirated or allowed to drain out by gravity or wall suction.

Common causes of GI bleeding include peptic ulcer disease, gastritis, and esophagitis and esophageal varices (Ricci, 1991). Patients undergoing an acute GI bleed are in a life threatening situation. Patients who have undergone a GI bleed resulting from cirrhosis and portal hypertension is at an added risk of bleeding from another lesion. This phenomenon could require a device that could be left in case of subsequent bleeding.

The care of patients undergoing a GI bleed is multi-focal, but nearly always involves the insertion of a nasogastric tube and resulting gastric lavage. Gastric lavage is a method used to confirm an active GI bleed. Beyond diagnostics, it also removes blood and clots from the stomach, facilitating endoscopy, and slowing the GI bleed and allowing the stomach to contract.

Drug overdoses, accidental or intentional, are common in many hospital emergency rooms. Gastric lavage continues to be the preferred and most thorough method for removing drugs which may be in the stomach. This is the only method that can be used in unconscious patients.

The present method for carrying out gastric lavage in most critical care units is cumbersome for nursing staff. The procedure has remained unchanged and is widely documented in medical/surgical and critical care procedure books. In the most common procedure a Salem Sump (NG tube) is inserted and attached to suction. The nurse must first disconnect the Salem Sump from the suction tubing. Following disconnection, a prescribed amount of fluid should be instilled through the Salem Sump with a 60-cc syringe. One may instill up to 500 cc of fluid through the NG tube. Once the prescribed fluid is instilled, the NG tube is then connected to suction. Alternatively, the nurse must manually aspirate the instilled fluid with the syringe and discard it in a bowl. Gloves are worn during the entire procedure. Due to the constant disconnection and connection of the tube and syringe, the nurse runs the risk of being contaminated with patient gastric secretions. As stated by Davis, the prior art of lavage is messy, non-sterile and time consuming (U.S. Pat. No. 4,872,866).

To simplify the procedure in hospital settings, double barrel syringes are part of the prior art. Walton (U.S. Pat. No. 3,818,907) consists of a double cylinder lavage syringe in which the two pistons are simultaneously operated. A check valve is designed to fill one cylinder with fluid from an I.V. while the other cylinder withdraws fluid from a body cavity. The cylinders are attached to a tube inserted into the body cavity. This system is complicated and not cost effective and not easily disposable. A problem with this device has been, the cross mixing of clean and waste fluid between the two cylinders.

Davis (U.S. Pat. No. 4,872,866) describes an improved method of lavage. Davis shows a device having side by side parallel irrigation and an aspiration cylinder encased in the rigid housing. Each cylinder contains a plunger extending from one end and irrigation check valves located at other ends. A septum joins the adjacent outer ends of the irrigation and aspiration check valve cylinders. This septum allows fluid streams flowing from the outer ends to flow together at an angle. A common exchange tube is attached to the housing. An exchange tube may be attached to the ends of the irrigation, the aspiration check valve cylinders and the septum. When either of the plungers is fully inserted into its respective cylinder, a seal on the end covers the respective inlet or outlet port making that cylinder inoperative. This prevents the cross mixing of clean and contaminated fluid from the two cylinders. While this device is an improvement upon the previous art, it continues to be large, complex, cumbersome and expensive. Due to it's size and the primary function of gastric lavage, the device may be removed following the lavage procedure.

U.S. Pat. Nos. 4,215,476 to Armstrong and 3,540,437 to Troy require use of specifically designed pump type apparatuses to perform the lavage procedure.

U.S. Pat. Nos 3,540,437 to Troy, 4,519,385 to Atkinson et al, 4,215,476 to Armstrong, and 4,282,873 to Roth disclose a system designed to provide a hand piece control for lavage.

Parham shows the use of interchangeable ports of similar design. None of these ports has a common opening to a central housing. Extensions 52 defeat the purpose of having the ports feed to a common opening to the medial housing. The housing of this patent is more general, and is not designed to have an elastic contact with a cooperating syringe.

None of the prior art suggests using elastic connections or ports to form tight seals with hypodermic syringes. This compares with seals which may be pierced, such as those shown in Fink.

The present invention provides that these seals which may be pierced may be used or opened for using a hypodermic syringe. When opened, these seals which may be pierced remain attached by flexible arms. These seals which may be pierced may be closed again after use.

The separation between elastic manual connections and non-elastic powered drains is important for diverse uses. Example may generally be grouped as gross versus fine drainage and insertion, cross draining is too quick for some sampling and may not give sufficient control. In addition, to control, the proposed structure allows for (1) the introduction of chemicals while doing lavage, or (2) sampling while withdrawing lavage. In order to have better mixing of chemicals and more precise samples, the invention provides a first and second medial port having a common point of mixing, sampling and intersection. This is found with the specification in the area designated 24 in the medial port fixture. This is important since it allows for injected medications to be mixed directly into the flowing lavage to insure all of the medication reaches the destination at the desired rate, properly mixed. It also allows for samples to come from the same source, untainted and unobstructed.

Clegg, U.S. Pat. No. 5,057,093 shows a device having an elastic, flexible cylinder 68a. This device has an elastic strap 72a holding a plug 76a having a common passage with a separate cylinder 34 having a separate plug 74 with a separate strap 70. This may have a diameter which is gradually reduced to provide a variable fit.

The modification of the function of seals, such as those in the prior art Berch, Parham and Manska, is not obvious. The function of the seal has not been previously suggested.

The prior art shows the medial selection as opening alternatively two medial ports. These two medial ports may go to a distal opening or the proximal opening. Compare FIG. 7 of Manska which is provided for transduction and Parham which shows ports in a series without a common opening. This common opening is necessary to make sure medication is administered into the same flow and that samples are taken from the same flow. The prior art does not suggest, nor would it be consistent with the disclosure in the prior art to have the multiple medial ports sealable or opened independently in conjunction with a three way valve. In Kaiser; U.S. Pat. No. 2,854,027; the patent describes the use of a three-way valve in the prior art fashion. As can be seen, the juncture of sampling, etc. is controlled by the three way valve. This is different. In the current specification there is no valve interfering with communication between the two medial ports shown.

Kaiser discloses an elastic seal for a syringe end 24 or tube end 23 together with a three-way valve. The Flock disclosure allows for the medial seals to be opened and closed. The medial seals may be used with a variety of introducing or sampling devices of separate sizes. The medial openings may be connected directly to the syringe or tube. Since the seals never come completely detached, the process is simplified. The elimination of Parham type serial ports and common opening assists in mixing effluent.

Lopez may be distinguished. Lopez does not provide multiple ports and does not allow for a coarse mechanical lavage with a constant mechanized source of suction or fluid input. Nor does it have medial ports having the structural connection with the flow of suction or fluid input described above.

The main focus of any discussion of the difference between the cited prior art and the present invention lies in the structural connection of the elastic medial ports to a three-way valve capable of selecting the medial ports. A more narrow embodiment would include the structural, water tight connection of these medial ports around a syringe or tubing or within a syringe or tubing. Two different sizes for the medial openings may be provided to receive different, but common lavage accessories. The different sizes provide for receiving different types of syringes or tubes.

An object of the adapter is to provide a means of lavage that is disposable, simple, comparatively inexpensive and simplifies lavage without mixing fluids with a valve that incorporates directional flow of fluid or secretions.

Another object of this disclosed invention is that it does not require a special pump device and can be used with a variety of gravity, portable or wall suction units routinely provided by health care institutions.

An object of this device is to provide a means of lavage that is simple, comparatively inexpensive and facilitates lavage without mixing fluids through the use of a valve that incorporates directional flow of fluid or secretions. At the same time, the device allows for careful mixing of fluids in a medial chamber. Similarly, the device allows for careful sampling of fluids from the same chamber. All of this may be accomplished without leaks or disconnection of hoses which poses a health risk.

Another object of this device is that it may remain in place following the actual lavage procedure. The small size and adaptability to functions other than lavage allows the device to remain in place. A manual valve allows the selected direction of the flow of fluid or secretions through different ports. At least one port has a common reservoir for mixing or sampling.

This device includes a valve that controls directional flow of fluid or secretions through proximal and distal instillation and removal ports as well as a medial port. The medial port separates into two separate ports of different size used for instillation or removal of fluid.

Once the position of the valve is changed, thereby changing the directional flow of fluid or secretions, the operators hands may remain free. It is unnecessary for the operator to hold the device during the instillation or removal of fluid or secretions.

Another object of this device is to provide for adaptability. This device may be used for a variety of systemic procedures involving gastric, urinary, rectal and subcutaneous intraperitoneal tubes and catheters.

GENERAL DISCUSSION OF THE INVENTION

This device has a medial elastic infusion port to simplify the attachment of syringes and tubes used during lavage. At least one manually operable valve controls the flow path of fluid through a hollow passageway. The valve is positioned in the center of the hollow lumen of the adapter.

Both distal and proximal ports of the hollow lumen of the adapter may be graduated to enhance the connection into a variety of tubing styles. The proximal port is connected to tubing inserted into a body cavity. The distal graduated port may be connected to drainage or suction devices.

The valve is designed to be manually shifted from a position that obstructs the flow of fluid through the lumen to one that allows the flow of fluid. The fluid flows through one of several openings or ports of the adapter. The medial port coalesces into two different size ports, at least one of which is elastic. This medial port is positioned between the two end ports and provides another access for fluid instillation or withdrawal per syringe.

The valve controls directional flow of fluid or secretions. The device may remain in place following the actual lavage procedure to simplify further suction, drainage or additional lavage in case of continued need for lavage.

The invention is designed to utilize the variety of gravity, portable or wall suction units routinely provided by health care institutions without cross mixing of fluids in conjunction with syringe applications through the use of the valve that incorporates directional flow of fluid or secretions, luer lock fittings and at least one elastic fitting. The elastic fitting may be constructed of rubber or other elastic material. The material is preferably of a type which can cooperate with the tubing or syringe attached to the elastic fitting to make the attachment water tight.

The operators hands may remain free except to change the position of the valve, it is unnecessary for the operator to hold the device during the instillation or removal of fluid or secretions.

It is therefore an object of the invention to provide a valve that incorporates directional flow of fluid or secretions through proximal and distal instillation and removal ports where at least one port is elastic.

It is a further object to provide for medial ports of different sizes and functions used for the instillation or removal of fluid and secretions that may be necessary for different techniques.

It is a further object of the invention to provide for a closed system of irrigation and drainage of fluid and body secretions through a variety of existing tubes and catheters inserted into body cavities. This decreases the risk of transfer of potentially harmful patient secretions to the care giver.

These and other objects and advantages of the invention will become better understood after this from a consideration of the specification with reference to the accompanying drawings forming part thereof, and in which like numerals correspond to parts throughout the several views of the invention.

Another object of this device is it's simplicity and size. This contributes to cost containment in health care.

Another object of this device is that it provides for a closed system of irrigation and drainage of fluid and body secretions through the connection of the device to a variety of existing tubes and catheters inserted into body cavities. By use of this closed system, it affords the operator a means of performing lavage and decreasing the risk of transfer of potentially harmful patient secretions to the care giver.

DETAILED DISCUSSION OF THE PREFERRED EMBODIMENT(S)

Figure 1:
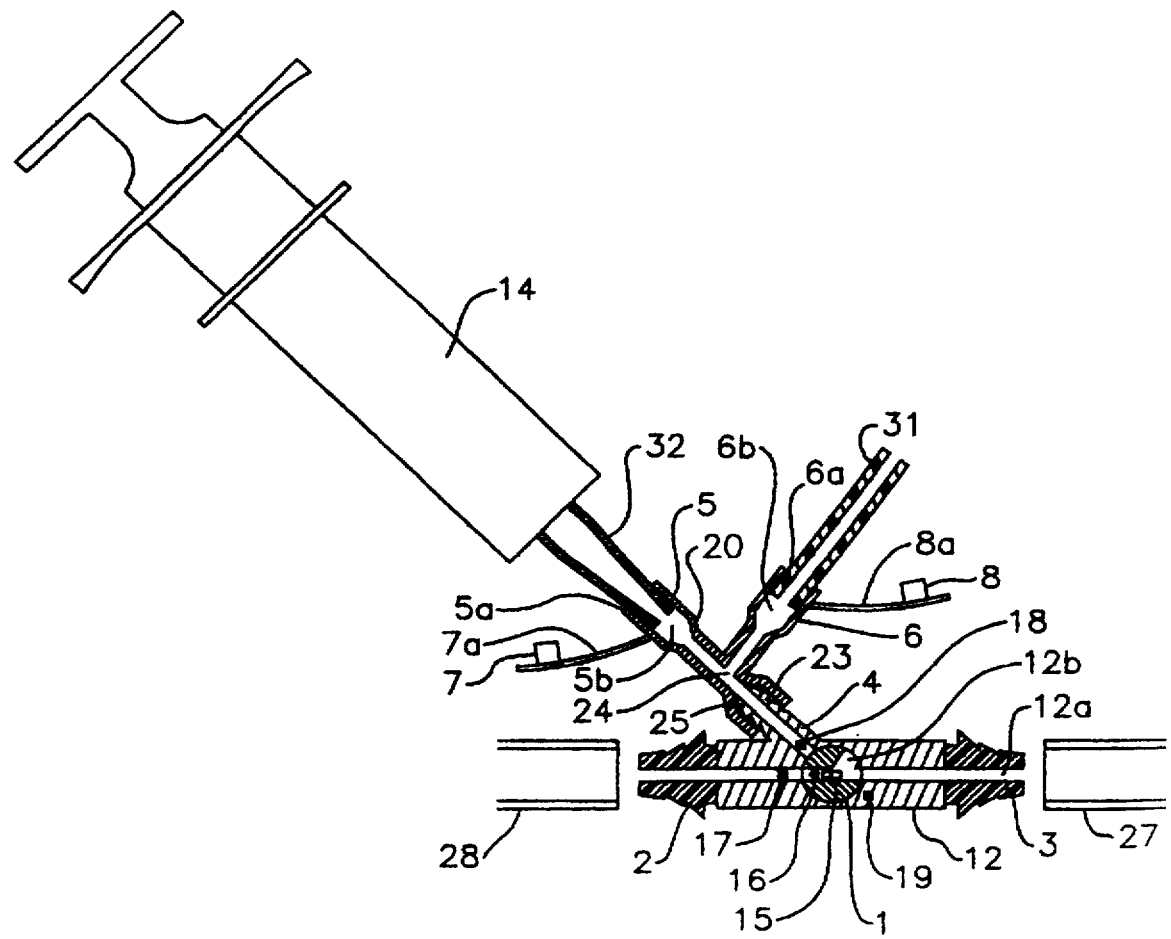
FIG. 1 is a cross sectional view of the preferred embodiment showing two equivalent medial openings with syringe suction and tube feeding.

As can best be seen by reference to FIG. 1, the invention comprises a housing or linear body 12 defining a tubular canal 12(a). Housing 12 has a distal end 2 defining a distal opening 2(a), a proximal end 3 defining a proximal opening 3(a) and a medial end 4 defining a medial opening 4(a). The proximal end 3 is the end closest to the patient. The proximal end comprises a proximal connecting means 3 for connecting tubing that is preferably a luer lock 3. The distal end comprises a distal connecting means 2 for connecting tubing that is preferably a luer lock 2.

The medial end 4 of the housing 12 defines a medial channel 4(b) leading to a medial opening 4(a). The medial opening 4(a) in the preferred embodiment opens into a medial luer Lock fitting 23. The housing 12 so described is essentially rigid in construction.

The medial end 4 may be angled toward the patient as shown in FIG. 1 to ease flow between the medial end 4 and the proximal end 3.

A flexible medial attachment means 20 connects to the medial luer lock 23 by way of a flexible medial attachment cylinder 25 which fits over the luer lock 23.

This medial attachment cylinder 25 communicates with common chamber 24. A flexible first cylinder 5, defining a first cavity 5(b), and a flexible second cylinder 6, defining a second cavity 6(b), communicate with the common chamber 24.

The first cylinder 5 and second cylinder 6 define a first opening 5(a) and second opening 6(a) which may have a frustoconical shape to allow for the insertion of various medical devices as described in more detail below.

Figure 5:
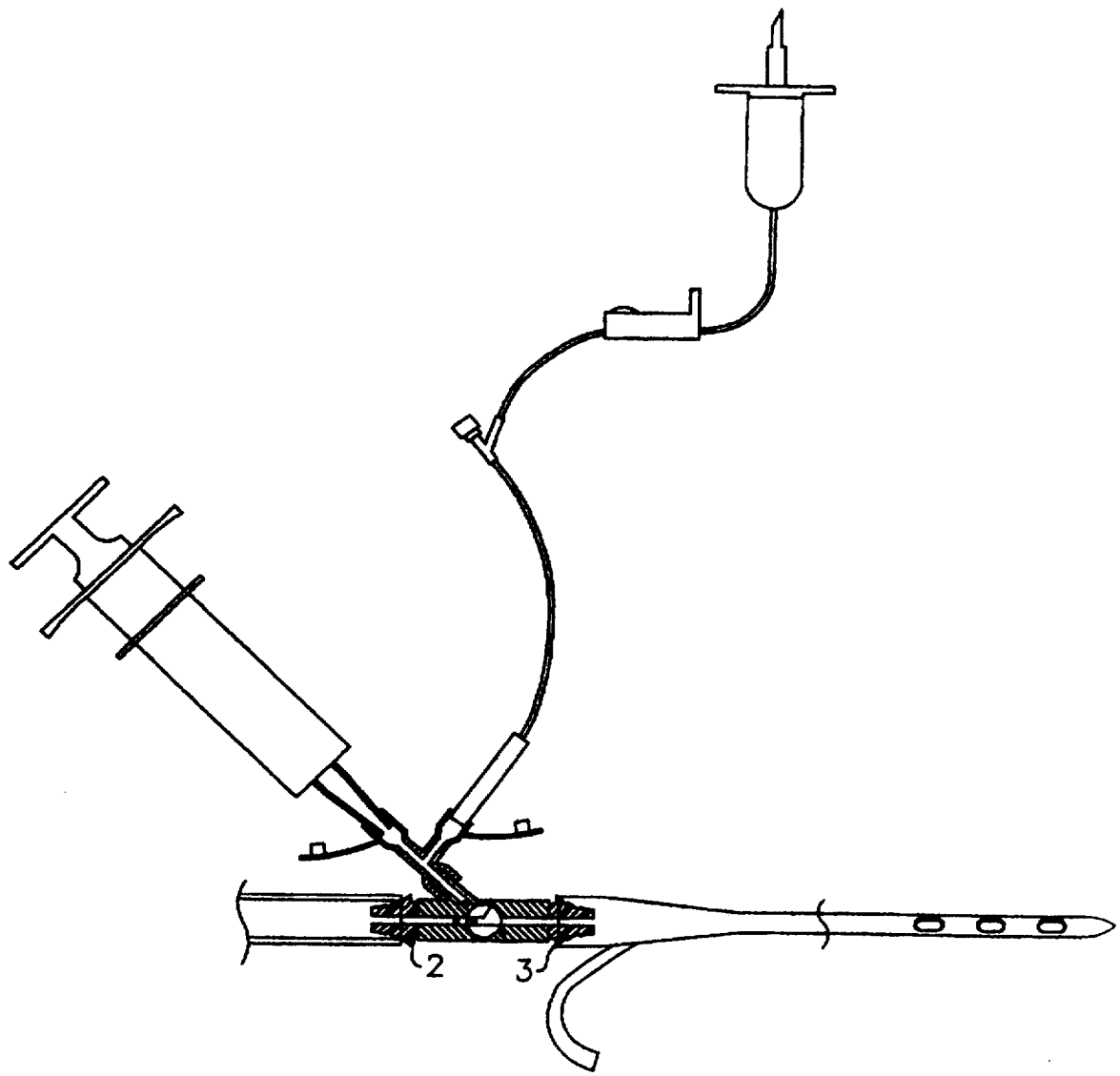
FIG. 5 is a less detailed view of the embodiment shown in FIG. 1 showing more of the attachments used in conjunction with the invention.

In FIG. 1, first opening 5(a) receives a 60 cc syringe 14 having a tip 31 which inserts into the flexible first opening 5(a). This connection between tip 31 and opening 5(a) is substantially water tight. Also shown in FIG. 1, and in greater perspective in FIG. 5 is a drip line 31 inserted into the second opening 6(a) with the same water tight fit. To accommodate different devices, the shape and size of cylinders 5 and 6 may vary as described in more detail below.

The tubular canal 12(a) defines a selection chamber 12(b) which contains a valve 1 capable of directing flow through the tubular canal 12(a) selectively to the medial end 4 or the proximal end 3 selectively from the distal end 2.

In the preferred embodiment, the first cylinder cavity 5(b) has a frusto-conical shape so that the fit is increasingly snug as the syringe tip 32 which has a corresponding shape is inserted. In FIG. 1, the opening 6(a) has a cylindrical inner circumference that corresponds to a standard drip line 31.

In all of the embodiments, the medial end 4 serves as a flexible attachment for providing water tight seals between rigid insertion devices (drip line 31, tip 32) and a rigid three way valve 1.

In the preferred embodiment, openings 5a and 6a may be sealed by inserting first plug 7 into the first cylinder 5 and second plug 8 into the second cylinder 6. The first plug 7 is connected to the first cylinder 5 by way of an elastic strap 7(a). The second plug 8 is attached to the second cylinder 6 by way of an elastic strap 8(a).

In the preferred embodiment the cylinders 25, 5 and 6, as well as all other elements of the medial attachment means 20 are made of elastic material such as rubber. This allows for air tight seals and simplifies connecting the cylinders. This also simplifies the removal of a syringe or tube (such as the drip line 31). Finally, it allows for the housing 12 to be cleaned separately from the medial attachment means 20 where the medial attachment means can be molded from a single unit and attached or removed from a luer lock fitting 23.

Standard surgical tubing 27 attaches to the proximal end 3. Standard surgical tubing 28 attaches to the distal end 2. The tubing 27 runs into the patient utilizing whatever type of insertion is required.

As can best be seen by reference to FIG. 1, the knob 15 for controlling the valve 1 is preferable marked with directional control 16. Control 16 may be aligned with distal mark 17 or medial mark 18. The markings show what port is open to the proximal port. There may be a stop mark 19 that shows that the valve is closed to all ports.

As can be seen, the medial suer lock may be replaced with a tube for cementing or otherwise attaching the base 50 of the first cylinder 5.

The second flexible cylinder 6 has a second opening 6(a). This second opening 6(a) has an external circumference corresponding to a standard 3 cc luer lock syringe 14. A 3 cc luer lock syringe may be inserted over the cylinder 6.

Figure 3:
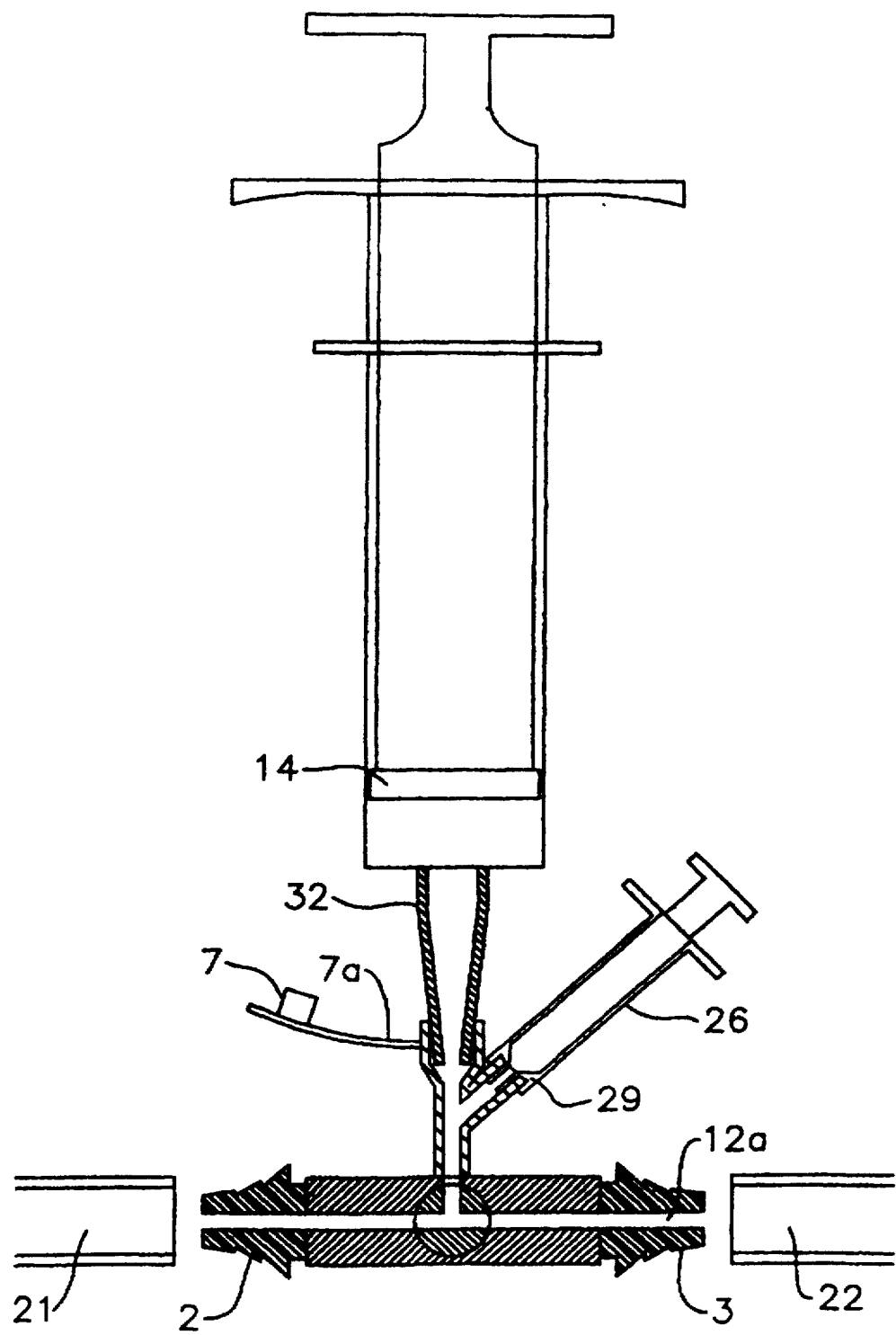
FIG. 3 is a cross sectional view of an alternative embodiment showing the use of syringe suction with a luer lock syringe 14.

Second plug 7 or first plug 8 may be pierced to allow injection of fluids. These plugs can be used to occlude the port openings 5 and 6 when the openings are not in use. FIG. 3 shows an embodiment where the second seal 7 is an integral part of the second cylinder 6. This embodiment does not require the second cylinder 6 be flexible. It may be used to inject medication through a seal or plug 7 which may be pierced. This seal or plug 7 is attached to the cylinder 6.

In the preferred embodiment shown in FIG. 1, the cylinders 7 and 8 are preferably made of a single mold from elastic materials.

To simplify cleaning, the medial cylinders 7 and 8 may be detachable. This is because in the medial cylinders are made of flexible materials it may be more cost effective to dispose of this rather than cleaning.

Valve 1 may be made multidirectional to allow for three way operations. FIG. 1 shows the outline of the fluid path for the housing 12 and the valve 1.

Figure 2:
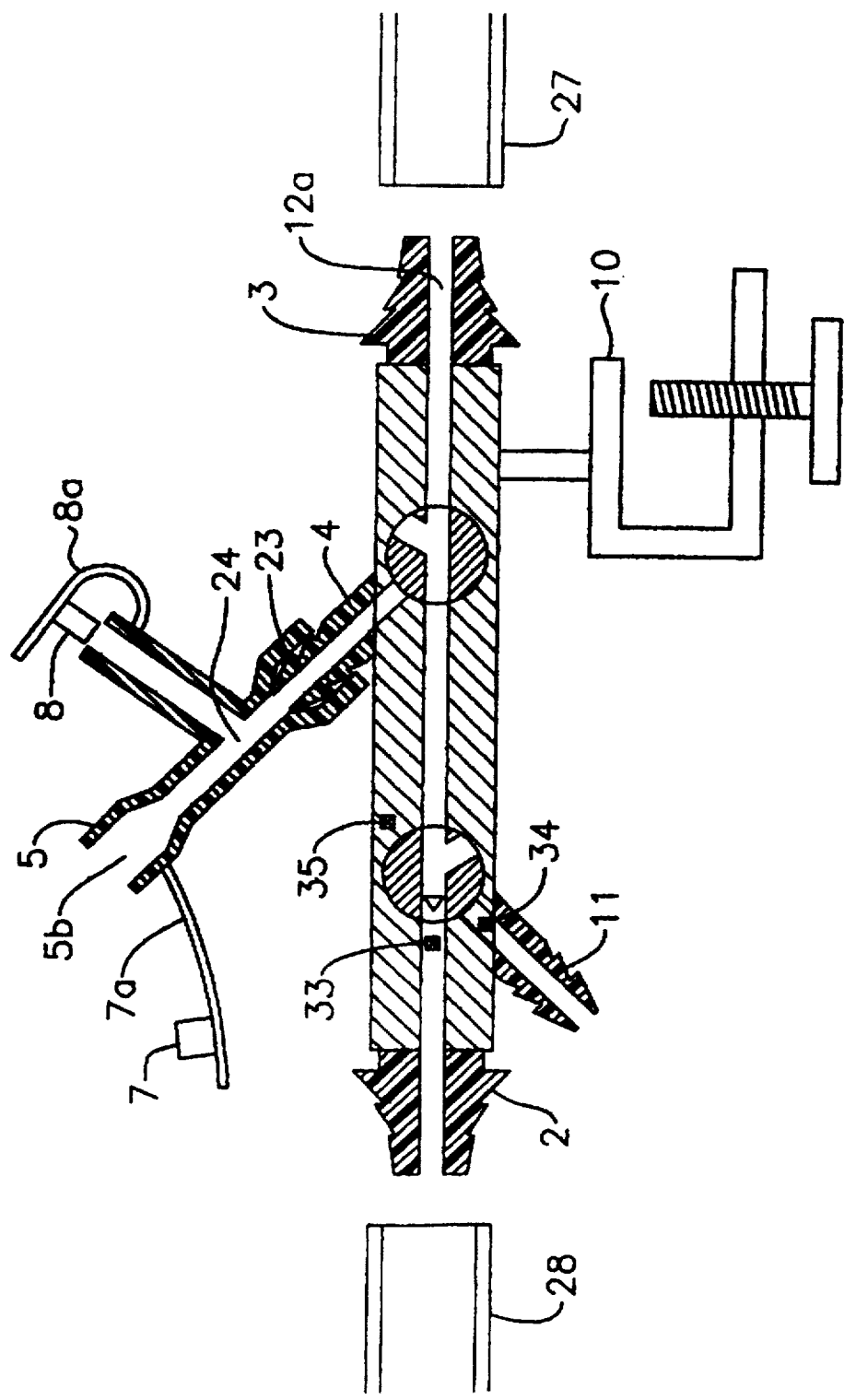
FIG. 2 is a cross sectional view of an alternate embodiment using a distal valve in addition to a medial valve.

FIG. 2 shows an embodiment having a second three way valve 13 leading to a second distal end 11. This second valve 13 is similarly marked to the first valve 1. It has a second control 22 pointing to the first distal opening mark 33, second distal opening mark 34 and closed position 35. This valve 13 is also important because it allows for the distal end to be closed completely.

As shown in FIG. 2, a mounting 10 may be provided to affix the device onto an IV stand (not shown).

FIG. 2 shows that cylinders 5 and 6 need not have the same shape. FIG. I shows a similar shape which may be desirable when using two separate large GU type 60 cc syringes. In FIG. 2, a straight second cylinder 6 is shown. In this way, it can be seen that different flexible medial attachments may be substituted onto the housing 12 at the medial location 4.

The second distal opening 11 may be provided for suction while distal opening 2a is used for application of fluids. This would allow the user to have fewer lines to disconnect while still having medial port 4 available for other purposes.

By having potentially separate pressure ports for high pressure and hand controlled suction, without utilizing a greater degree of handling, the user can switch between the two types of suction. One source of suction may be for sampling and the other for greater control of the lavage.

FIG. 3 shows a slightly different arrangement. The perpendicularly attached flexible attachment means 20 is directly attached to the housing 12 eliminating the luer lock 23. This embodiment would be a more disposable version.

This embodiment shows a 3 cc luer lock syringe 26 having a fitting 29 which inserts both over and within the cylinder 6. In this way a water tight seal is provided on the inside and outside of the cylinder 6.

Figure 4:
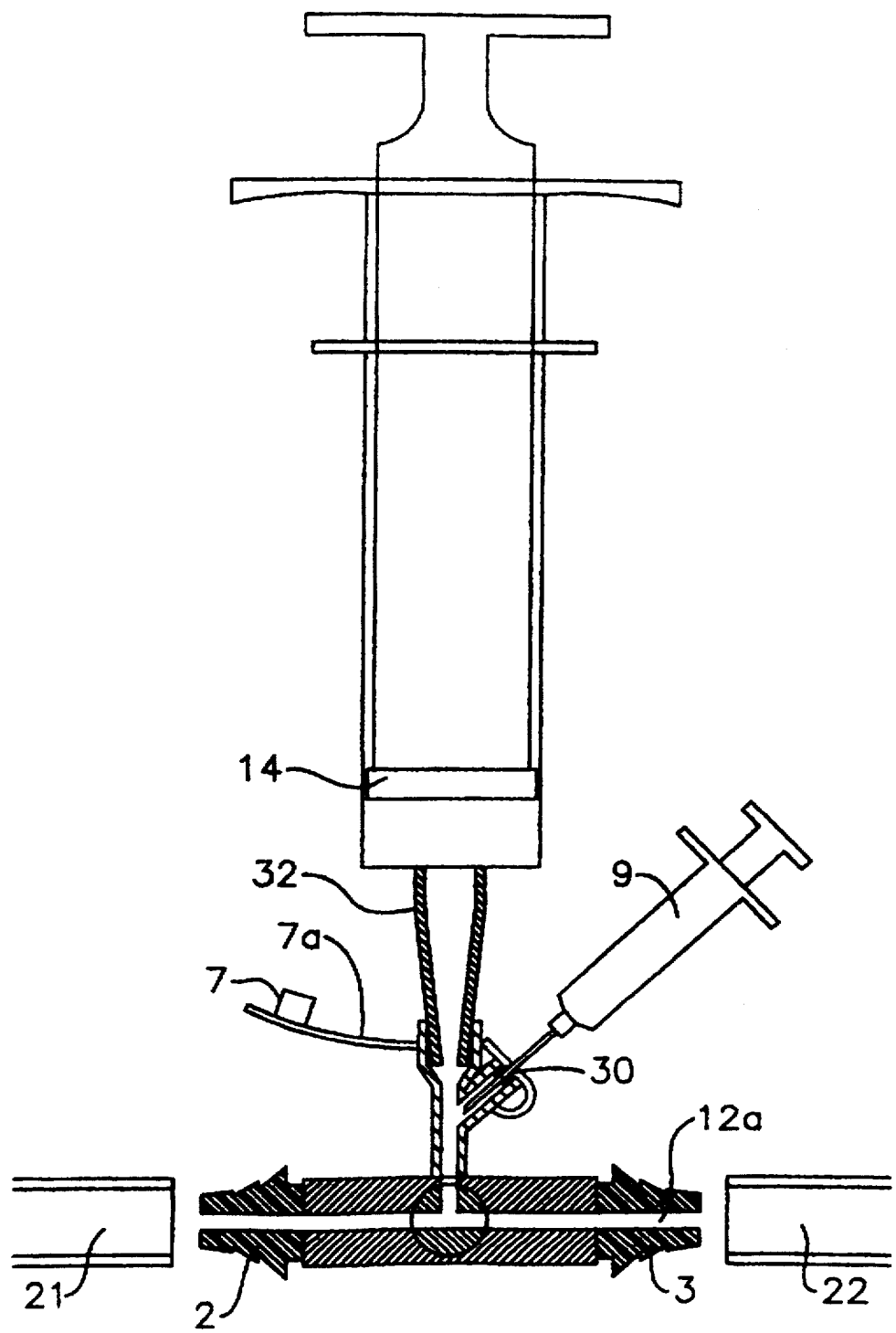
FIG. 4 is a cross sectional view of an alternative embodiment showing a syringe with a needle.

FIG. 4 shows where medial port 6 is sealed with plug 8 and is pierced by hyperdermic needle 30. A syringe 9 has needle 30 inserted into ports 6 for injecting medication or sampling while port 5 has a separate syringe for insertion fluids or draining fluids.

FIG. 5 shows where distal tubing 21 is applied to the distal end for suction or flooding. Also shown is the proximal end tubing 22 which is attached to a fitting to go into the patient's body cavity (not shown) for lavage. The Luer locks 2 are generally sufficient to hold tubing in place to practice this invention.

The method of using the device so disclosed may be set out as follows:

(1) determining the type of lavage necessary;

(2) inserting into the body cavity the appropriate appliance attached to tubing as is known in the art;

(3) determining the source between at least the distal and medial openings for application of fluid;

(4) attaching the appliance for providing fluid to the Medial port or distal port as determined by the user;

(5) selecting the valve setting to direct fluid from the source into the proximal port;

(6) filling the body cavity with an amount of fluid by activating a means for applying fluid available to the user such as a pump driving fluid from a bag or insertion by way of syringe;

(7) selecting the means for suction;

(8) attaching the means for suction to either the appropriate distal end or the medial end;

(9) selecting the valve setting to direct the vacuum to the appropriate end to which the means for suction is attached;

(10) applying suction and

(11) repeating the steps 1–10.

As can be seen by reference to FIGS. 1, 2 and 3 and the disclosure, the device may be left in place on a patient. It may be used intermittently unless an unacceptable amount of bacteria or other impurity is introduced into the system. Likewise, because of the simplicity of the device it may be thrown away, in whole or in part, or cleaned using sterile techniques for reuse.

Because many varying and different embodiments may be made within the scope of the inventive concept herein taught and because many modifications may be made in the embodiment(s) herein detailed in accordance with the descriptive requirements of the law, it is to be understood that the details herein are to be interpreted as illustrative and not in a limiting sense.

We claim:

1. An apparatus for facilitating lavage with hookup to flexible tubes and to substantially rigid medical devices such as rigid tubing, needles or syringe tips comprising;

(a) a substantially rigid housing defining a canal within the housing, said canal having a selection chamber said chamber being continuous with a proximal end, a distal end, and a medial end and said selection chamber being located at the intersection of the distal end, medial end and proximal end and wherein the proximal end defines a proximal opening; the distal end defines a distal opening and the medial end defines a medial opening;

(b) and wherein said housing further comprises a medial connecting means located about the medial opening; and further comprising;

(c) an elastic flexible medial attachment means attached to the medial connecting means and wherein said flexible medial attachment means defines a common chamber continuous with the medial opening and further defines an opening for insertion of a substantially rigid medical device;

(d) and wherein said selection chamber further comprises a selection means within the selection chamber for directing flow between the medial opening, proximal opening and distal opening.

2. The device of claim 1 wherein the flexible medial attachment means further comprises at least one first flexible cylinder of elastic material defining a first cylinder cavity functionally opening to the common chamber and defining an inner circumference and depth of substantially the same size as the outer circumference of the substantially rigid medical devices and wherein the depth is sufficient to allow adequate insertion of the rigid medical device so as to provide a substantially water tight seal between the elastic connecting means and the substantially rigid medical device.

3. The device of claim 1 wherein the flexible medial attachment means further comprises at least one flexible cylinder of elastic material defining a first cylinder cavity functionally opening to the common chamber and defining an an outer circumference and depth of substantially the same size as the inner circumference of the substantially rigid medical devices and wherein the depth is sufficient to allow adequate insertion of the rigid medical device over the at least one cylinder so as to provide a substantially water tight seal between the elastic connecting means and the substantially rigid medical device.

4. The device of claim 2 wherein the elastic connecting means further comprises a second elastic flexible cylinder defining a second cylinder cavity communicating with the common chamber and having seal means so as to provide a substantially water tight seal between the second elastic flexible cylinder and a second substantially rigid medical device.

5. The device of claim 1 wherein the selection means is a rotatable valve located within the selection chamber defining passages to direct the flow within the selection chamber from the distal end to either the proximal opening or medial opening or neither.

6. The device of claim 1 wherein the elastic flexible medial attachment means further comprises at least one non-elastic connecting means defining a chamber continuous with the common chamber.

7. The device of claim 1 wherein the medial attachment means further comprises an elastic strap having a first end and a second end and wherein the first end is connected to the medial attachment means and the second end further comprises a first plug having an insertion end defining an outer circumference of substantially the same size as the inner circumference of the opening so that the elastic first plug may fit within the opening to form a substantially air tight seal to close off the opening.

8. The device of claim 4 wherein the first flexible cylinder and the second flexible cylinder have a different inner circumference.

9. The device of claim 4 wherein the first flexible cylinder and the second flexible cylinder have a different outer circumference.

10. The device of claim 4 wherein the first cylinder further comprises an inner circumference corresponding to the outer circumference of a GU type 60 cc syringe.

11. The device of claim 1 further comprising a mounting means attached to said body for affixing the rigid housing to an IV stand or similar apparatus.

12. The device of claim 2 wherein the first flexible cylinder defines a first cylinder cavity having a frustoconical shape which expands in size as the first cylinder cavity travels away from the common chamber so as to allow for a variably tight fit as the rigid medical device is inserted within the cavity.

13. The device of claim 1 wherein the tubular canal further defines a distal select chamber at the distal end and wherein the distal end further comprises a distal selection means for closing off the tubular canal between the distal end and the selection chamber.

14. The device of claim 13 further comprising a second distal opening and a distal channel continuous with the second distal opening and the distal select chamber and wherein the distal selection means further comprises a channel for directing the flow from either the first distal opening or the second distal opening to the medial portion of the tubular canal.

15. The device of claim 2 wherein the at least one flexible cylinder further comprises a plug covering the opening which plug may be pierced by a needle.

16. The device of claim 1 wherein the medial connecting means further comprises a medial leur lock continuous with the medial opening and wherein the medial attachment means further comprises a medial attachment chamber continuous with the common chamber which may fit over the medial leur lock to form a substantially water tight fit.

17. The device of claim 1 wherein the proximal end and distal end luer lock fittings.

* * * * *